(12) United States Patent
Dach

(10) Patent No.: US 6,403,790 B1
(45) Date of Patent: Jun. 11, 2002

(54) PROCESS FOR THE PRODUCTION OF EPINASTINE HYDROCHLORIDE IN THE HIGH-MELTING CRYSTAL MODIFICATION

(75) Inventor: Rolf Dach, Gau-Algesheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/716,355

(22) Filed: Nov. 20, 2000

(30) Foreign Application Priority Data

Dec. 3, 1999 (DE) .......................... 199 58 460

(51) Int. Cl.$^7$ ........................... C07D 487/04

(52) U.S. Cl. ..................................... 540/579

(58) Field of Search ............... 514/214.02; 540/579

(56) References Cited

U.S. PATENT DOCUMENTS 4,313,931 A * 2/1982 Walther et al. ............... 424/45
5,312,916 A * 5/1994 Schneider et al. ........... 540/579

FOREIGN PATENT DOCUMENTS

WO    WO-97/17971    * 5/1997

* cited by examiner

Primary Examiner—John M. Ford
(74) Attorney, Agent, or Firm—R. P. Raymond; T. X. Witkowski

(57) ABSTRACT

A process for preparing epinastine hydrochloride of formula (I)

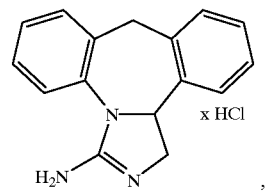

(I)

the process comprising:
(a) suspending and dissolving an epinastine base of formula (II)

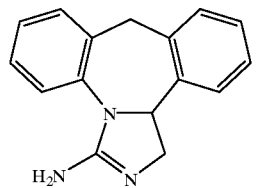

(II)

in water by the addition of aqueous hydrochloric acid at a pH of ≧7;
(b) extracting the aqueous solution obtained from step (a) with an organic, water-immiscible solvent;
(c) removing the organic, water-immiscible solvent from the aqueous solution obtained from step (b); and
(d) adjusting the pH of the aqueous solution of step (c) to ≦6 using hydrochloric acid to precipitate the product of formula (I), and then drying the product.

22 Claims, 1 Drawing Sheet

PROCESS FOR THE PRODUCTION OF EPINASTINE HYDROCHLORIDE IN THE HIGH-MELTING CRYSTAL MODIFICATION

The invention relates to a process for preparing epinastine hydrochloride in the high-melting crystal modification.

BACKGROUND OF THE INVENTION

The compound epinastine (3-amino-9,13b-dihydro-1H-dibenz-[c,f]imidazolo[1,5-a]-azepine) belongs to the 2-aminoimidazolines and is a therapeutically active substances characterized primarily by its antiallergenic and antihistaminergic activity (EP 35749).

Methods of preparing epinastine hydrochloride are known from the prior art. In EP 35749, epinastine hydrochloride is obtained by precipitation from a methanolic solution with ether. DE 41 02 148 discloses the formation of epinastine hydrochloride by reaction of the free epinastine base with HCl in dimethyl formamide. The abovementioned processes for preparing epinastine hydrochloride which are known from the prior art do, however, have some disadvantages. Thus, epinastine hydrochloride cannot always be prepared in pure form using these methods or it is obtained in various crystal modifications. One known modification melts at about 250° C. to 263° C. (low-melting crystal modification) and another melts at about 275° C. to 281° C. (high-melting crystal modification). The use of alcohols in the precipitation of epinastine hydrochloride proposed in EP 35749 results in a loss of quality because of gradual decomposition of the product. In this process, the product also contains up to about 5% of the low-melting crystal modification, according to DSC (Differential Scanning Calorimetry). The process for preparing epinastine hydrochloride disclosed by DE 41 02 148 involves the use of dimethyl formamide, which can only be removed from the product of the process at high temperatures during drying, because of its high boiling point. As a result, the product begins to melt to some extert and changes color. In addition, drying on an industrial scale requires an unacceptably high energy consumption. Finally, dimethyl formamide has been classified as being damaging to the fetus, which means that its presence in a pharmaceutical composition has to be avoided at all costs.

Figure 1:
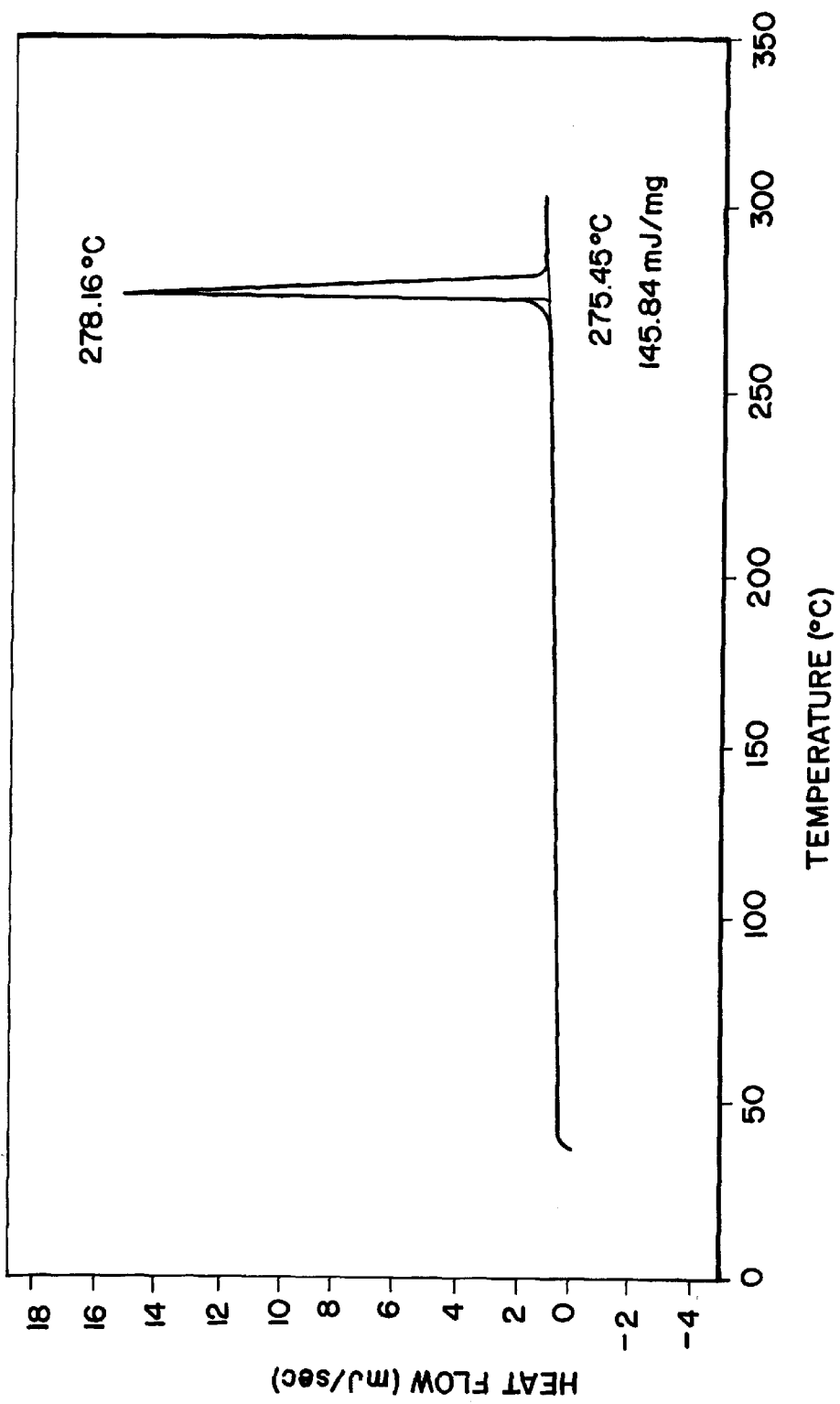
FIG. 1 is a Differential Scanning Calorimetry (DSC) graph of an epinastine hydrochloride product made according to the process of the invention.

One aim of the present invention is to provide a process for preparing epinastine hydrochloride which avoids the disadvantages occurring in the processes known in the prior art.

Detailed Description of the Invention

The invention relates to a process for preparing epinastine hydrochloride (formula I) (3-amino-9,13b-dihydro-1H-dibenzo-[c,f]imidazolo[1,5-a]azepine-hydrochloride) in the high-melting crystal modification starting from epinastine base (II) according to Diagram 1.

Diagram 1:

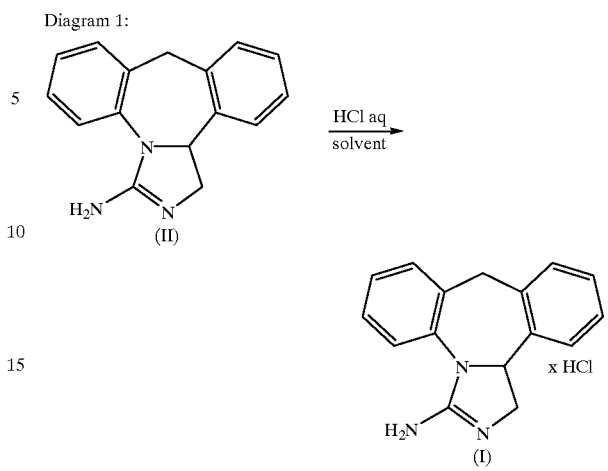

Another aim of the present invention is to provide a process for preparing epinastine hydrochloride which leads only to the formation of epinastine hydrochloride in the high-melting crystal modification. With regard to the pharmaceutical use of epinastirie hydrochloride in conjunction with the statutory requirements for the quality control of pharmaceutical products, it is absolutely essential that pharmaceutical compositions containing epinastine hydrochloride should contain this active substance only in a single crystal modification.

The process according to the invention relates to the preparation of epinastine hydrochloride of formula (I)

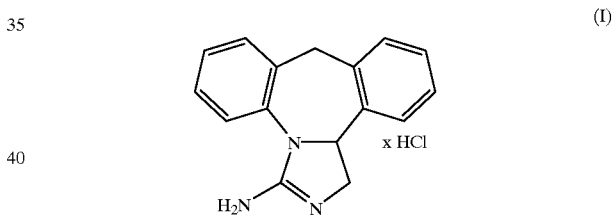

caracterized by means of a process comprising the steps of:

(a) a first step in which epinastine base of formula (II)

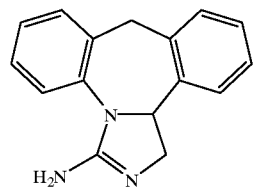

is suspended in water and dissolved by the addition of aqueous hydrochloric acid at a pH of $\geq 7$;

(b) a second step in which the aqueous solution obtainable from the first step is extracted with an organic, water-irnniscible solvent and the extraction agent is subsequently removed; and (c) a third step in which the product of formula (I) is precipitated from the aqueous solution obtained by means of the second step by the addition of hydrochloric acid at a pH of $\leq 6$ and then dried.

According to the invention, the following procedure is preferably used. In a suitably sized reaction vessel, epinastine base (II) is suspended in water and dissolved at between 20° C. and 90° C., preferably 40° C. to 80° C., particularly preferably at 50° C. to 70° C. by the addition of aqueous hydrochloric acid at a pH which should not fall below 7. At the same time, care should be taken to make the pH acidic enough for the epinastine base (II) to dissolve in water, but for the pH to remain basic enough to ensure that the epinastine hydrochloride (I) is not yet precipitated. Preferably, the pH of the solution is between 7.5 and 9; a pH of 8 is particularly preferred. The hydrochloric acid is preferably used in concentrated from, the term "concentrated form" meaning an approximately 32% by weight aqueous hydrochloric acid.

The solution thus obtained is then extracted with the organic, water-immiscible solvent. Suitable solvents include, for example, halogenated hydrocarbons such as methylene chloride, carbon tetrachloride, esters such as, for example, ethyl acetate or butyl acetate, ethers such as dimethyl or diethyl esters, or other organic solvents known from the prior art for the extraction of aqueous phases. Preferably, organic esters are used, especially butyl acetate.

The solution is extracted at least once, preferably several times, with the organic solvent. After the organic solvent has been separated off, any residual amounts of the organic solvent in the aqueous phase are removed by azeotropic distillation. Therefore the organic solvents used for the extraction are preferably those which can be removed from water by azeotropic distillation.

Activated charcoal is added to the resulting aqueous solution in the warm and is filtered off again after some time. Preferably, the mixture is stirred for some time at a temperature of between ≧50° C. and 100° C., preferably between 70° C. and 95° C., most preferably at 80° C. to 90° C.

After filtration, the clear solution is cooled to below 50° C. and the pH is adjusted to ≦6 with hydrochloric acid, preferably concentrated hydrochloric acid. The pH is preferably adjusted to 3 to 5, most preferably 3.5 to 4.5. The temperature of the solution should not fall below 25° C., so as to prevent premature crystallization of the product. The temperature is preferably maintained between 30° C. and 40° C. As soon as the desired pH has been achieved, the solution is carefully cooled with stirring, preferably to about 20° C. After a few minutes, the product (I) is spontaneously precipitated, with the development of heat, which should be removed by cooling.

After crystallization is complete, which may if desired by accelerated and/or completed by cooling, the crystal slurry is filtered off and washed with water. Ice water is preferably used for the washing. The product is then dried.

Any unprecipitated product still present in the filtrate can be precipitated using methods known from the prior art.

The product obtained by this process is pure epinastine hydrochloride (I) in the higher-melting crystal modification, according to the usual methods of analysis.

With the process according to the invention it is possible to obtain yields of the product (I) in the higher-melting crystal modification of over 80% of theory.

If the purity of the product does not meet the particular requirements, the process can be repeated. If necessary, the last stages are repeated.

The advantage of the process according to the invention is that, compared with the process known from the prior art, dimethyl formamide is totally replaced by water. This advantageously improves the pharmaceutical quality of the product (I), since among other things the product does not contain any residual traces of dimethyl formamide or its breakdown products and the product can be dried at moderate temperatures.

EXAMPLE

Epinastine base (124.5 g) is suspended in a defined amount of water (390 ml) and the pH is adjusted to 8 at a temperature of 60° C. by the addition of 32% hydrochloric acid (about 50 ml). After the aqueous solution has twice been extracted with butyl acetate at 60° C. (1.50 ml and 75 ml) and the organic phase has been separated off, some of the water is distilled off under normal pressure in order to eliminate the residual butyl acetate azeotropically. Then activated charcoal (LX-Ultra, moistened with water) is added to the residue at about 90° C., this is stirred for 30 minutes and the product solution is then filtered till clear and the charcoal filtered off is washed with about 12.5 ml of water. Hydrochloric acid is metered into the clear filtered solution at 30° C. to 40° C. until a pH of 3.5 to 4.5 is obtained (about 1 ml), it is then cooled to 20° C. and inoculated with epinastine hydrochloride (containing water of crystallization and moistened with water). After about 5 to 10 minutes, a thick crystal slurry forms, while the temperature rises slightly.

To complete the crystallization, the mixture is stirred for about another 30 to 45 minutes at 20° C., then cooled to 0° C. to 5° C. in 1 to 2 hours, stirred for another 30 minutes at 0° C. to 5° C., the crystals are suction filtered and washed with ice-cold water (about 100 ml).

The yield is 86.8% of theory. This can be increased to 90% of theory by recovering an after-yield.

According to the DSC plot in FIG. 1 the product obtained is the desired high-melting modification of epinastine hydrochloride.

What is claimed is:

1. A process for preparing epinastine hydrochloride of formula (I)

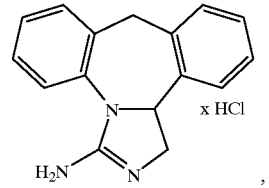

(I)

the process comprising:

(a) suspending and dissolving an epinastine base of formula (II)

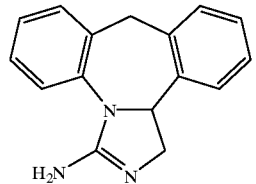

(II)

in water by the addition of aqueous hydrochloric acid at a pH of ≧7;

(b) extracting the aqueous solution obtained from step (a) with an organic, water-immiscible solvent;

(c) removing the organic, water-immiscible solvent from the aqueous solution obtained from step (b); and (d) adjusting the pH of the aqueous solution of step (c) to $\leq 6$ using hydrochloric acid to precipitate the product of formula (I), and then drying the product.

2. The process according to claim 1, wherein the suspension of the epinastine base of formula (II) is combined with the hydrochloric acid in step (a) at a temperature of between 20° C. and 90° C.

3. The process according to claim 1, wherein the pH at the end of step (a) is between 7.5 and 9.

4. The process according to one of claims 1, 2 or 3, wherein the organic, water-immiscible solvent is a halogenated hydrocarbon, an ether, or an ester.

5. The process according to one of claims 1 to 3, wherein the removal of the organic, water-immiscible solvent in step (c) is accomplished by decanting, by azeotropic distillation, or by both decanting and azeotropic distillation.

6. The process according to one of claims 1 to 3, wherein between steps (c) and (d), the aqueous phase obtained by step (c) is purified using activated charcoal at a temperature of between 50° C. and 100° C.

7. The process according to claim 6, wherein the purification of the aqueous phase obtained by step (c) using activated charcoal is performed at a temperature of between 70° C. and 95° C.

8. The process according to claim 6, wherein the purification of the aqueous phase obtained by step (c) using activated charcoal is performed at a temperature of between 80° C. to 90° C.

9. The process according to one of claims 1 to 3, wherein in step (d), the pH is adjusted to between 3 to 5.

10. The process according to claim 9, wherein the pH is adjusted to between 3.5 to 4.5.

11. The process according to one of claims 1 to 3, wherein in step (d), the hydrochloric acid is added at a temperature of 25° C. to 50° C.

12. The process according to claim 1, wherein the suspension of the epinastine base of formula (II) is combined with the hydrochloric acid in step (a) at a temperature of between 40° C. and 80° C.

13. The process according to claim 1, wherein the suspension of the epinastine base of formula (II) is combined with the hydrochloric acid in step (a) at a temperature of between 50° C. and 70° C.

14. The process according to one of claims 1, 2, or 3, wherein the organic, water-immiscible solvent is selected from the group consisting of methylene chloride, carbon tetrachloride, ethyl acetate, butyl acetate, dimethyl ether, and diethyl ether.

15. The process according to claim 4, wherein between steps (c) and (d), the aqueous phase obtained by step (c) is purified using activated charcoal at a temperature of between 50° C. and 100° C.

16. The process according to claim 5, wherein between steps (c) and (d), the aqueous phase obtained by step (c) is purified using activated charcoal at a temperature of between 50° C. and 100° C.

17. The process according to claim 4, wherein in step (d), the pH is adjusted to between 3 to 5.

18. The process according to claim 5, wherein in step (d), the pH is adjusted to between 3 to 5.

19. The process according to claim 6, wherein in step (d), the pH is adjusted to between 3 to 5.

20. The process according to claim 4, wherein in step (d), the hydrochloric acid is added at a temperature of 25° C. to 50° C.

21. The process according to claim 5, wherein in step (d), the hydrochloric acid is added at a temperature of 25° C. to 50° C.

22. The process according to claim 6, wherein in step (d), the hydrochloric acid is added at a temperature of 25° C. to 50° C.

* * * * *

UNITED STATES PATENT AND TRADEMARK OFFICE
CERTIFICATE OF CORRECTION

PATENT NO. : 6,403,790 B1
DATED : June 11, 2002
INVENTOR(S) : Rolf Dach

It is certified that error appears in the above-identified patent and that said Letters Patent is hereby corrected as shown below:

<u>Column 1,</u>
Line 42, "extert" should read -- extent --.

<u>Column 2,</u>
Line 25, "epinastirie" should read -- epinastine --.
Line 45, "caracterized" should read -- characterized --.
Line 63, "irnniscible" should read -- immiscible --.

Signed and Sealed this

Twenty-third Day of July, 2002

*Attest:*

JAMES E. ROGAN
*Attesting Officer*     *Director of the United States Patent and Trademark Office*